United States Patent [19]
Graf et al.

[11] Patent Number: 5,012,798
[45] Date of Patent: May 7, 1991

[54] ORTHESIS FOR THE TRIDIMENSIONAL REDUCTION OF SCOLIOSES

[76] Inventors: Henry Graf, 8, rue Duquesne, 69006 Lyon; Gérard Dauny, 15, rue des Murgers, 21240 Savigny-les-Beaune, both of France

[21] Appl. No.: 498,104
[22] Filed: Mar. 23, 1990
[30] Foreign Application Priority Data Mar. 23, 1989 [FR] France .................. 89 03833

[51] Int. Cl.⁵ .............................................. A61F 5/02
[52] U.S. Cl. ........................................ 128/78; 128/68
[58] Field of Search ................... 128/78, 869, 870, 68, 128/95.1, 96.1; 606/54

[56] References Cited
U.S. PATENT DOCUMENTS

| | | | |
|---|---|---|---|
| 1,935,859 | 11/1933 | Putz | 128/78 |
| 4,202,327 | 5/1980 | Glancy | 128/78 |
| 4,559,933 | 12/1985 | Batard et al. | 128/78 |
| 4,688,558 | 8/1987 | Hooper, Jr. et al. | 128/78 |

FOREIGN PATENT DOCUMENTS 277336 11/1913 Fed. Rep. of Germany ........ 128/78

Primary Examiner—Richard J. Apley
Assistant Examiner—Jennifer L. Doyle
Attorney, Agent, or Firm—Scully, Scott, Murphy & Presser

[57] ABSTRACT

A dynamic orthosis device for the tridimentional reduction of scoliosis wherein two elastically deformable plastic hands joined at the anterior laterally enclose the thorax of the patient. The hands assembly is connected to a pelvic girdle by at least two lateral supports made of elastically deformable semirigid material. As the rear of the hand, which are not attached, are expanded outward due to the movement of the thorax patient the lateral supports provide a torsional return stress which forces the hands to create a pressure on the body of the patient. This pressure is beneficial in reeducating the spine of the patient and thereby reducing scoliosis.

6 Claims, 3 Drawing Sheets

ORTHESIS FOR THE TRIDIMENSIONAL REDUCTION OF SCOLIOSES

The present invention relates to an orthosis for the tridimensional reduction of scolioses.

It is known that scoliosis can be analyzed as a segmental deformation of the trunk, each segment comprising a gibbosity on one side and a counter-depression on the other side. Each segment is articulated on the adjacent segment via an oblique line, described by Dr. CHENEAU as being a neutral line (see CHENEAU-MUNSTER publication). This neutral line corresponds in radiological terms to the junction point defined by Mr. PERDRIOLLE and by Doctor GRAF (see Perdriolle: "La scoliose, son étude tridimensionnelle" [Scoliosis, its tridimensional study], Graf: "Mécanique de la courbe scoliotique" [Mechanics of the scoliotic curve"]).

In order to reduce such scolioses, various types of corsets have already been proposed, comprising elements in the form of plates, which are called "hands" in the specialist field, which stress parts of the thorax or of the back of the patient in order to straighten the vertebral column and return it to the vertical position, while exerting on the vertebrae a de-rotation and elongation effect, in order to compensate the pivoting and sagging of the vertebrae which appear in scoliosis.

The "hands" of such corsets are adjustable in position, in order to be able to modulate and adapt their action as the reduction of the scoliosis progresses. However, they are purely "passive" in the sense that they are fixed in position relative to the body of the patient and exert on the latter a simple pressure of which the direction of application and the magnitude of the force are not modulated as a function of the respiratory cycle.

The present invention aims to improve the corsets of this type by proposing an orthosis which, during the inspiration phase of the respiratory cycle of the patient, opposes the natural expansion of the thoracic cage at the front by forcing the patient to stoop, which brings the dorsal spine into the kyphosis position, in order thereby to normalize the vertebral position.

More precisely, the invention aims to provide an orthosis for the tridimensional reduction of scolioses which, during the inspiration phase of the respiratory cycle, forces the patient to stoop, when the shoulder blades move away from one another, and forces his vertebral column to straighten, with an opposite effect on expiration. This permanent effect of movement of the orthosis, prompted by the patient himself, results in an active re-education of the spine.

During their distancing phase, the supports impose upon the hands rotation-compression movements whose aim is an untwisting of the segments lying above and below the junction point relative to each other.

The object of the invention is consequently an orthosis for the tridimensional reduction of scoliosis, which orthosis comprises:

firstly, two lateral hands of an elastically deformable plastic material, intended to enclose laterally the thorax of the patient, with a front part arranged to the front of the thorax and a rear part arranged to the rear of the latter, these hands being attached at the front by joining means which prevent them from moving away from one another, while the rear parts are free to be displaced relative to one another when they are stressed by the thorax during the respiratory cycle;

secondly, a pelvic girdle intended to be made secure to the pelvis of the patient;

finally, two lateral supports of an elastically deformable semi-rigid material, which connect respectively in the vertical direction one of said hands and the corresponding part of the pelvic girdle, with a view to exerting a torsional return stress on the rear parts of the hands when the latter move away from one another in the phase of inspiration of the thorax of the patient.

A lumbar support made of plastic material can be added; this hand can be active or passive.

It is understood that, the hands being connected by front joining means, while the rear parts are free to be displaced elastically, the orthosis forces the spontaneous respiratory movements of the patient to be applied to the rear, thereby recreating a physiological kyphosis favourable for the reduction of the scoliosis.

It will be possible for the hands of the orthosis to be of any material customary in the specialist field, for example rigid polyethylene. The joining means which connect them at the front can be simple straps. These adjustment means will preferably be adjustable in terms of position, in order to be able to make the hands secure to one another in a plurality of positions, as the reeducation of the patient progresses.

The supports will advantageously consist of bands of a carbon fiber composite, consisting of a thermoplastic resin reinforced with carbon fibers, preferably woven or braided, and can be fixed by means of rivets or the like on the hands and on the pelvic girdle.

The pelvic girdle can be of any type known per se.

In a preferred embodiment of implementation of the invention, the torsional return stress exerted by the lateral supports will be adjustable. For this purpose, the part of these supports separating a hand from the pelvic girdle will only be able to deform elastically in rotation over an adjustable part of its length. To this end, the supports will advantageously be backed along part of their length, from a hand and/or the pelvic girdle, by a rigid element adjustable in terms of position. This element or these elements will for example be mounted slidably on the supports and capable of being made secure to the latter in a plurality of positions, for example by means of screws or nuts. It will thus be possible to adjust the torsional return stress exerted by the lateral supports, when the hands are stressed during inspiration by the thorax of the patient and tend to move away from one another. In other words, it will be possible to adjust the stress to be exerted by the patient during natural inspiration, in order to move the rear parts of the hands away from one another.

These supports can have an adjustment in all positions at the level of the junction with the pelvic girdle.

The invention thus proposes a simple orthosis for tridimensionally reducing scoliosis, with which the patient himself stresses in a dynamic fashion, during inspiration, the hands intended to provide for the reeducation.

An embodiment of the invention will be described hereinbelow, by way of non-limiting example, with reference to the attached drawings. In these drawings.

Figure 1:
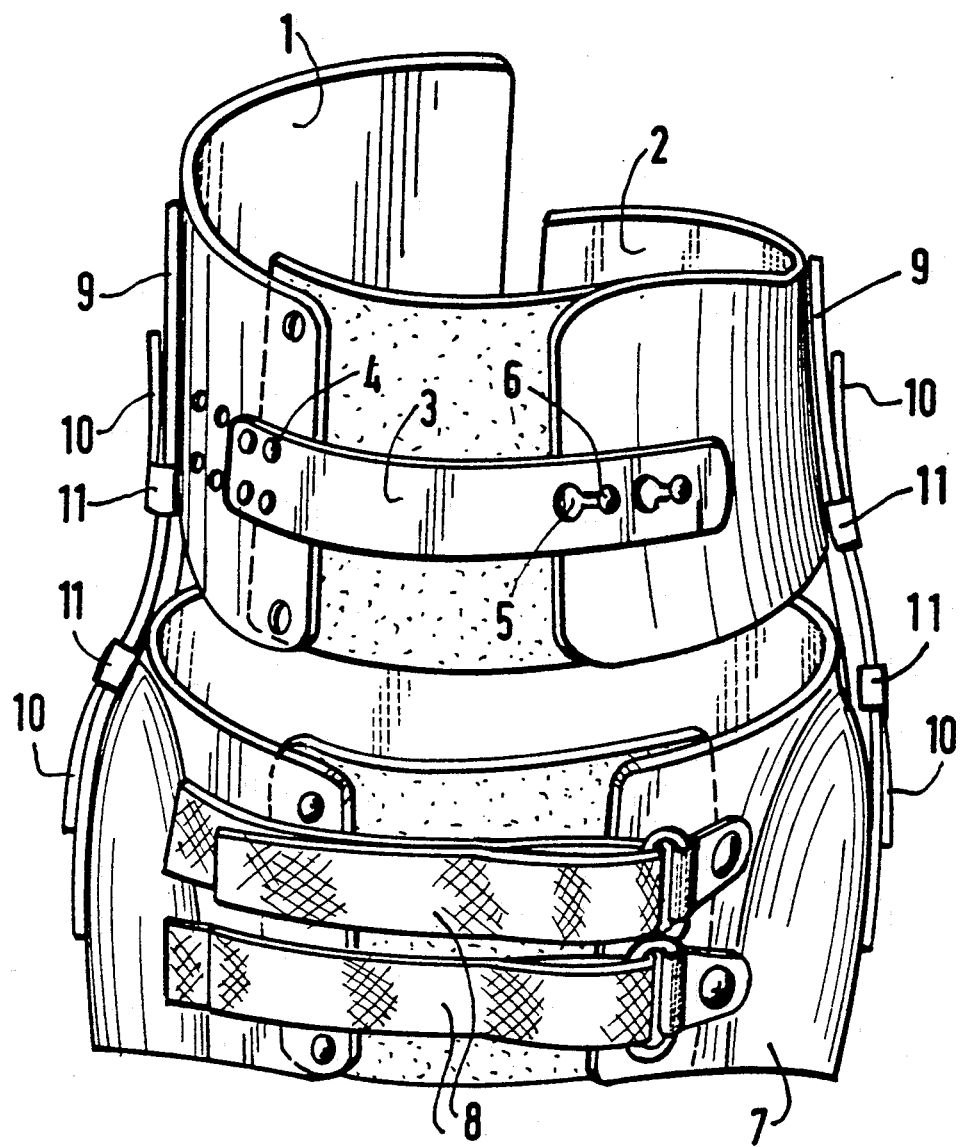
FIG. 1 is a front perspective view of the orthosis according to the invention.

As shown in the drawings, this orthosis comprises two curved-in plates 1, 2 of plastic material, called "hands", which match laterally the shape of the thorax of the patient, and whose front parts are secured to one another by a strap 3. This strap is fixed by means of screws 4 on the hands (sic) 1, and its other end comprises openings 5 in which there can be engaged in an adjustable manner one or more screwed buttons 6 projecting on the outer face of the hand. The rear parts of the hands 1 and 2 are mounted free to be displaced and, in particular, to move away from one another.

The orthosis also comprises a pelvic girdle, of a type known per se, comprising an open shell 7 whose front ends are connected in an adjustable manner by straps 8.

Supports 9 of an elastically deformable material, for example of carbon fiber composite, are arranged vertically in order to connect the lateral parts of the hands 1 and 2 and the pelvic girdle 7, on which they are fixed respectively by screws 14 and 15.

As has been explained hereinabove, during the inspiration movements of the patient, the strap 3 opposes the opening towards the front of the hands 1 and 2, despite the increase in volume of the thoracic cage, this forcing the patient to stoop, moving the rear parts of the hands 1 and 2 away from one another, thereby bringing the dorsal spine into the kyphosis position with a view to normalizing the position of the vertebral column.

During the inspiration movement of the patient, the opening of the hands 1 and 2 will thus impart a rotation to the supports 9, and the patient will have to fight against the return stress exerted by these supports.

Figure 2:
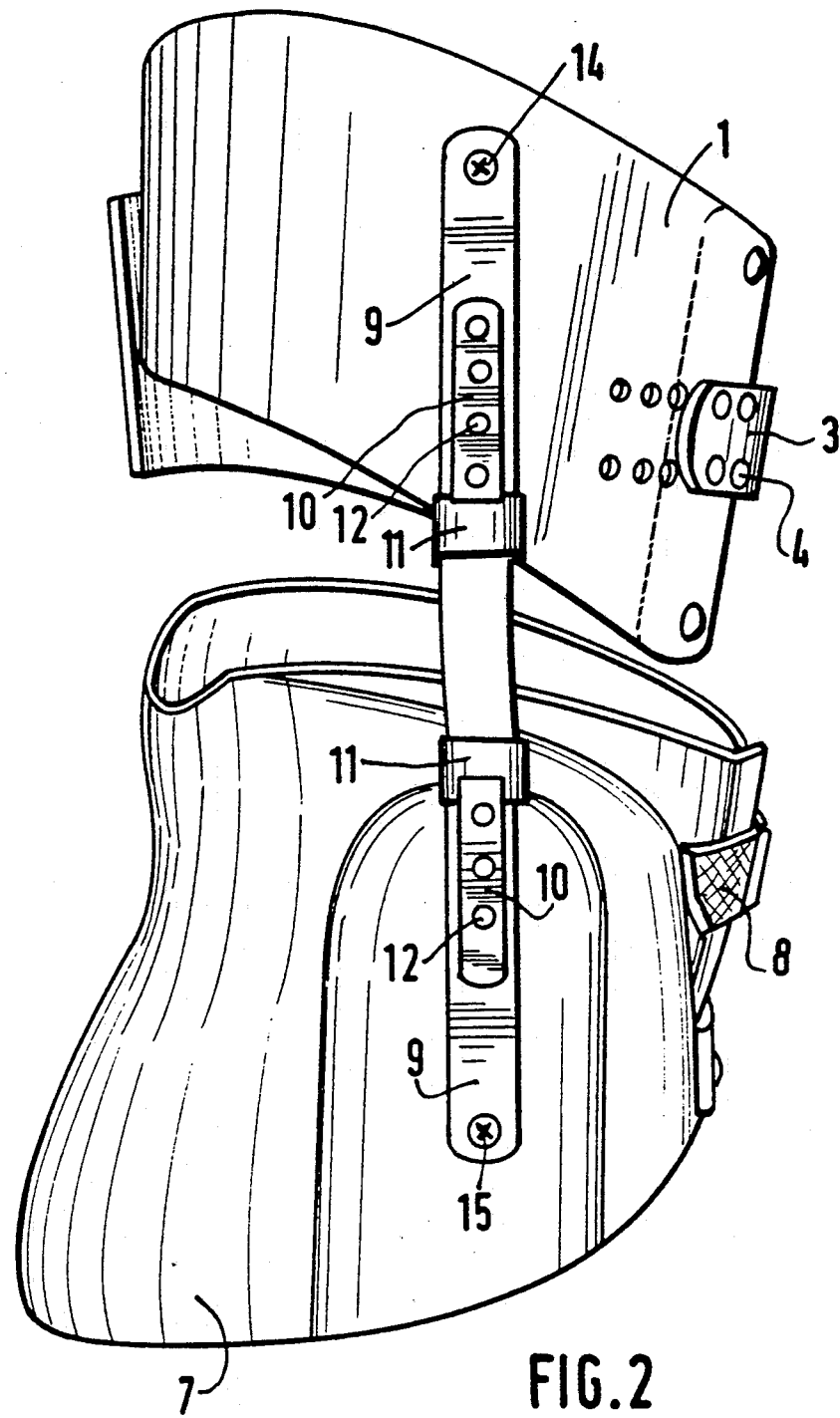
FIG. 2 is a side view of this same orthosis.
Figure 3:
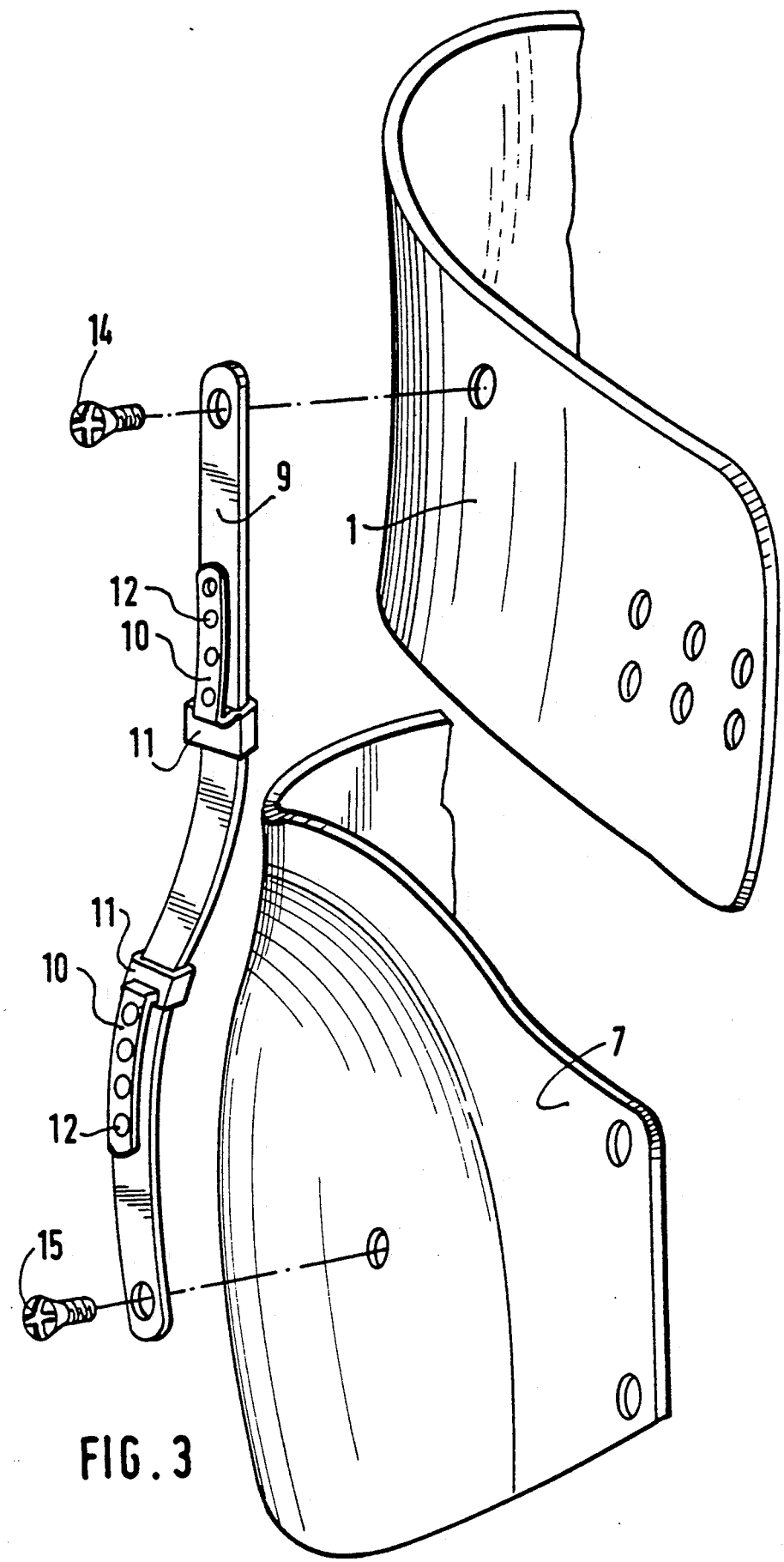
FIG. 3 is a partial exploded view of the latter.

In order to be able to adjust this stress, the part of the supports 9 capable of pivoting on itself will be limited and adjustable. For this purpose, as is seen more clearly in FIG. 2, each support 9 will be backed over part of its length, both from the hands 1 and 2 and from the girdle 7, with rigid bands 10 mounted slidably on the supports 9 by means of loops 11 and capable of being immobilized on these supports in a plurality of positions, by engaging screws 12 in openings in the bands 10. The only part of the supports 9 capable of being deformed, when it is subjected to a torsional couple, is thus the length separating the loops 11 and, the nearer these loops are to each other, the greater is the stress that the patient must exert during inspiration in order to pivot the supports and cause the distancing of the rear parts of the hands 1 and 2.

The invention thus affords a simple and adjustable means for tridimensionally reducing scolioses in a dynamic manner.

We claim:

1. An orthosis for the tridimentional reduction of scoliosis in a dynamic manner, which orthosis comprises:

firstly, two lateral hands (1, 2) of an elastically deformable plastic material, intended to enclose laterally the thorax of the patient, each hand with a front part arranged to the front of the thorax and a rear part arranged to the rear of the thorax, the front parts of these hands being attached by joining means (3) which prevent them from moving away from one another, while the rear parts are free to be displaced laterally relative to one another when they are stressed by the thorax during the respiratory cycle;

secondly, a pelvic girdle (7) intended to be made secure to the pelvis of the patient;

finally, at least two lateral supports (9) of an elastically deformable semi-rigid material, which connect respectively in the vertical direction one of said hands (1, 2) and the corresponding part of the pelvic girdle (7), for exerting a torsional return stress on the rear parts of the hands (1, 2) when the latter move away from one another in the phase of inspiration of the thorax of the patient.

2. THe orthosis as claimed in claim 1, wherein the means for joining the front parts of the hands (1, 2) is adjustable in terms of position.

3. The orthosis as claimed in one of claims 1 and 2, wherein the means for joining the front parts of the hands (1, 2) comprises a strap.

4. The orthosis as claimed in claim 1, wherein the supports (9) are equipped with a means for adjustment of their torsional return stress.

5. The orthosis as claimed in claim 4, wherein the means for adjustment of the torsional return stress of the supports (9) limits the length of the latter capable of being subjected to a torsional effect.

6. The orthosis as claimed in claim 5, wherein the means for adjustment of the torsional return stress of the supports comprises at least one rigid element (10) backing each support (9) over a part of its length from at least one of one said hand (1, 2) and said pelvic girdle (7), said rigid element being mounted slideably relative to the support (9) and capable of being fixed in a plurality of positions on the latter.

* * * * *